United States Patent [19]

Wildemeersch

[11] Patent Number: 4,708,134
[45] Date of Patent: Nov. 24, 1987

[54] INTRAUTERINE CONTRACEPTIVE DEVICE AND DEVICE FOR ITS INSERTION AND FIXATION TO THE UTERUS

[76] Inventor: Dirk A. A. Wildemeersch, Vossenhul 8, B-8300 Knokke-Heist, Belgium

[21] Appl. No.: 817,475

[22] Filed: Jan. 9, 1986

[30] Foreign Application Priority Data

Feb. 5, 1985 [BE] Belgium .................................. 214449

[51] Int. Cl.⁴ .............................................. A61F 5/46
[52] U.S. Cl. .................................................. 128/130
[58] Field of Search ............................. 128/127–131, 128/329 R, 330, 788; 604/891, 892; 63/2

[56] References Cited

U.S. PATENT DOCUMENTS 3,820,535  6/1974  Marco ................................. 128/130
3,954,103  5/1976  Garcia-Roel et al. .............. 128/130

Primary Examiner—Robert A. Hafer
Assistant Examiner—Kathleen D'Arrigo
Attorney, Agent, or Firm—Weingarten, Schurgin, Gagnebin & Hayes

[57] ABSTRACT

The invention relates to a new and improved intrauterine contraceptive device (IUD), which includes a fixing device to the fundal part of the uterine cavity, attached to members made in a material active into the uterine cavity, said members being attached the one behind the others, in a non-rigid assembly. The members are hollow members, open at both end and arranged in a sequence to form a longitudinal passage allowing passing through of a needle, and the fixing device to the fundal part of the uterine cavity is a thread affixed to the assembly of hollow members, provided with a retaining device in the uterine tissue, adapted for insertion by means of a needle.

The invention relates also to a device for the insertion and the fixation of such an IUD to the uterine wall which comprises a needle for inserting the retaining device interlocked to the thread in the uterine tissue, a member for protecting the needle and receiving the IUD, and an actuating member for the needle, movable in relation the protecting member. The needle passes through the passage of the IUD to engage the retaining device in the uterine tissue, and the internal cross section of the member for protecting the needle and receiving the IUD corresponds substantially with the outer cross section of the hollow members of the IUD.

12 Claims, 9 Drawing Figures

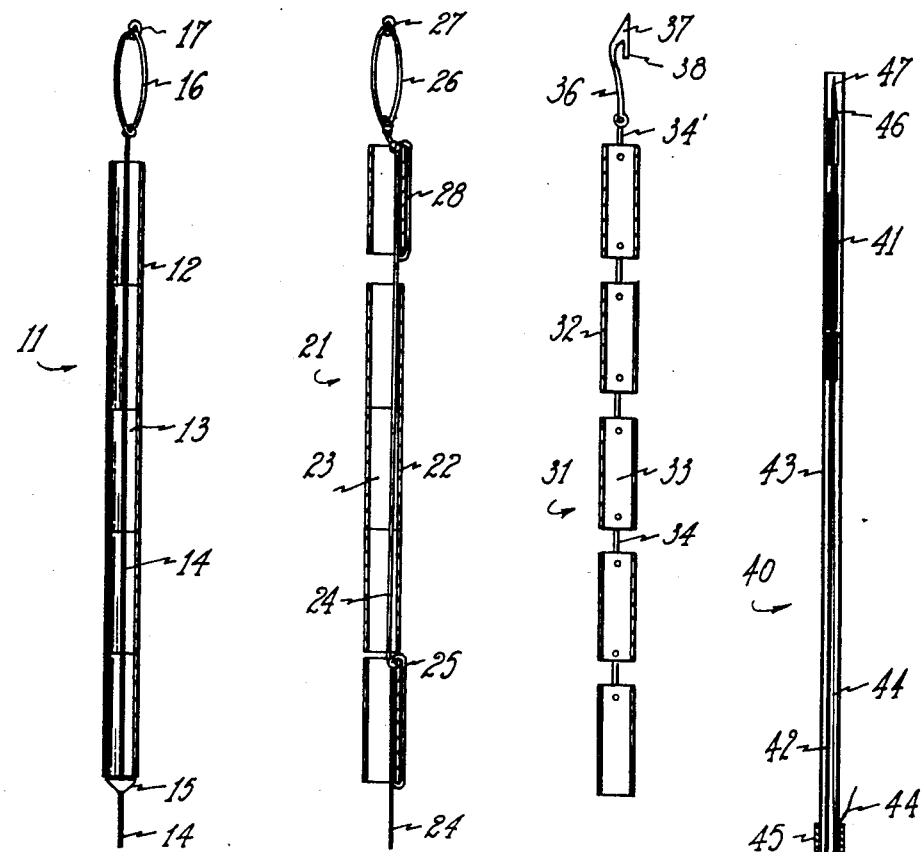
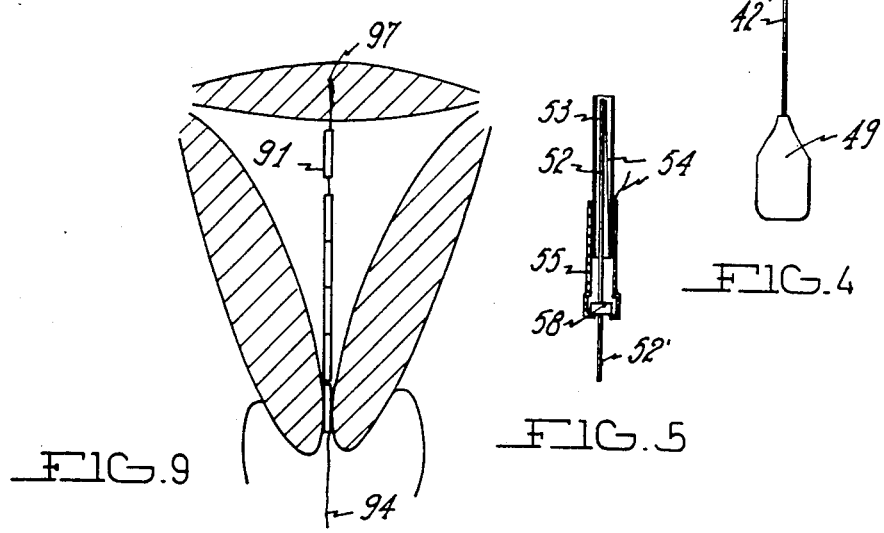

INTRAUTERINE CONTRACEPTIVE DEVICE AND DEVICE FOR ITS INSERTION AND FIXATION TO THE UTERUS

FIELD AND BACKGROUND OF THE INVENTION

The present invention relates to a new and improved intrauterine contraceptive device (IUD), remarkably well tolerated by the uterus and which is also very efficient due to its large effective copper surface area. Moreover, the special design of the IUD makes insertion thereof into the uterus easy, even for women who have never been pregnant, by means of an inserting device of very small diameter.

Most of the IUDs of the art are made of a plastic frame with a particular geometrical shape allowing its retention in the uterus, on which are brought copper wire or copper sleeves. The geometrical, generally T or Y type, shape of these frames, has been so designed as to allow adaptation thereof to the internal shape of the triangular uterine cavity. However, the diversity in size of the uterine cavities makes necessary an adaptation in size of the IUD to the size of the uterine cavity. Moreover, during uterine contractions, translocations of the IUD are always possible. Finally, it must be pointed out that the relative rigidity of such IUD often sets up tolerance problems, said rigidity frequently causing pain and bleeding problems, and even possibly hard damages to the uterus (perforation of the wall).

The contraceptive effectiveness of these IUDs depends largely on the surface area of copper and also on the correct position of the copper load in the uterus. In such IUD, it is generally admitted that about 60% of the copper area on the loop is effective, the remaining 40% being in contact with the frame, and having thus no contraceptive action. Moreover, when the IUD is out of its normal position the effect of the copper on the internal wall is uneven.

It has already been suggested in patent application EP-A-0100924 to design the IUD as a mere copper chain affixed to the top of the uterine cavity. An IUD of this kind has the advantage of having no specific shape and so being able to adapt itself without any stress to the modification of the uterine cavity. The IUD is thus perfectly tolerated and, as far as it is affixed to the midline of the uterus, it exerts a symmetrical action on the uterine cavity.

However the IUD decribed in patent application EP-A-0100924 has the drawback of using a complicated fixing device to the uterine wall, which does not authorize an easy withdrawal of the IUD, and which requires a rather bulky inserting device. Moreover, the copper surface area is small. Finally, as the time lapses, the copper dissolution may cause, by breakage of a link, the loss of a great part of, if not all, the copper load in the uterus, depending on the location of the breakage point in relation to the fixing device.

SUMMARY OF THE INVENTION

The aim of the present invention is to remedy to these drawbacks by providing an IUD which has a large effective copper surface area, which can be inserted into the uterine cavity, and fixed to the fundal part of the uterine cavity by means of a device having an extremely small cross-section, allowing its easy passage through the cervical canal, even for women who never were pregnant.

These goals are reached, according to the present invention, with an IUD including a fixing device to the fundus part of the uterine cavity, attached to members made in a material active into the uterine cavity, said member being attached the one behind the others in a non-rigid assembly, wherein the members in a material active into the uterine cavity are hollow members, open at both ends and arranged in a sequence to form a longitudinal passage allowing passing through of a needle, and wherein the fixing device to the fundal part of the uterine cavity is a thread, affixed to the assembly of hollow members, provided with a retaining device in the uterine tissue, adapted for insertion by means of a needle.

According to another characteristic feature of the invention the hollow members are stringed on the thread provided with a retaining device in the uterine tissue, and are retained at least by a stop means provided on the thread at the end opposite to the retaining device in the uterine tissue, the thread constituting assembling means for the members of the IUD, at least when the retaining device is inserted in the uterine tissue.

According to an additional characteristic feature of the invention, the stop means on the thread is made by the thread affixed to the remotest hollow member from the retaining device in the uterine tissue.

According to yet another additional characteristic feature of the invention, a second stop means is formed on the thread by fixing the thread to the closest hollow member to the retaining member, the interval between the two stop means allowing a loose interconnection of the hollow members.

According to another characteristic feature of the invention, for treatment of the uterus, the hollow members, or at least some of them, are made of a consumable material releasing an active substance for the treatment of the uterus.

According to yet another characteristic feature of the invention, the hollow members are interconnected by means of links achieving a non rigid assembly, and at least one of the hollow members or the links is attached to the thread provided with the retaining means to the uterus.

According to another characteristic feature of the invention, the hollow members are copper tubular members.

According to yet another characteristic feature of the invention, beyond the end opposite to the retaining device to the uterus, the IUD extends in a thread allowing traction on said retaining device to the uterus.

According to an additional characteristic feature of the invention, the thread allowing traction on the retaining device to the uterine tissue is the thread provided with the retaining device.

Another object of the invention is to provide a device for the insertion and the fixation to the uterus of an IUD according to the invention, which comprises a needle for inserting the retaining device interlocked to the thread in the uterine tissue, a member for protecting the needle and receiving the IUD, an actuating member for the needle, movable in relation to the protecting member, in which device the needle passes through the passage of the IUD to engage the retaining device in the uterine tissue, and the internal cross-section of the member for protecting the needle and receiving the IUD corresponds substantially with the outer cross section of the hollow members of the IUD.

DESCRIPTION OF THE DRAWINGS

These and other characteristics of the invention will be more readily understood when referring to the description as well as to the accompanying drawings which represent, merely by the way of examples, several embodiments of the invention, and in which:

FIG. 1 represents, in cross sectional view, one embodiment of an IUD according the invention, FIG. 2 represents, also in cross sectional view, another embodiment of an IUD according the invention, FIG. 3 is a cross sectional view of a third embodiment of an IUD according the invention, FIG. 4 shows, in a cross sectional view, a device for inserting an IUD into the uterus, FIG. 5 is a partial view of an alternative embodiment of the device shown in FIG. 4, FIG. 9 is a schematic cross sectional view of the uterus in which an IUD according to the invention has been placed.

DETAILED DESCRIPTION

Figure 6:
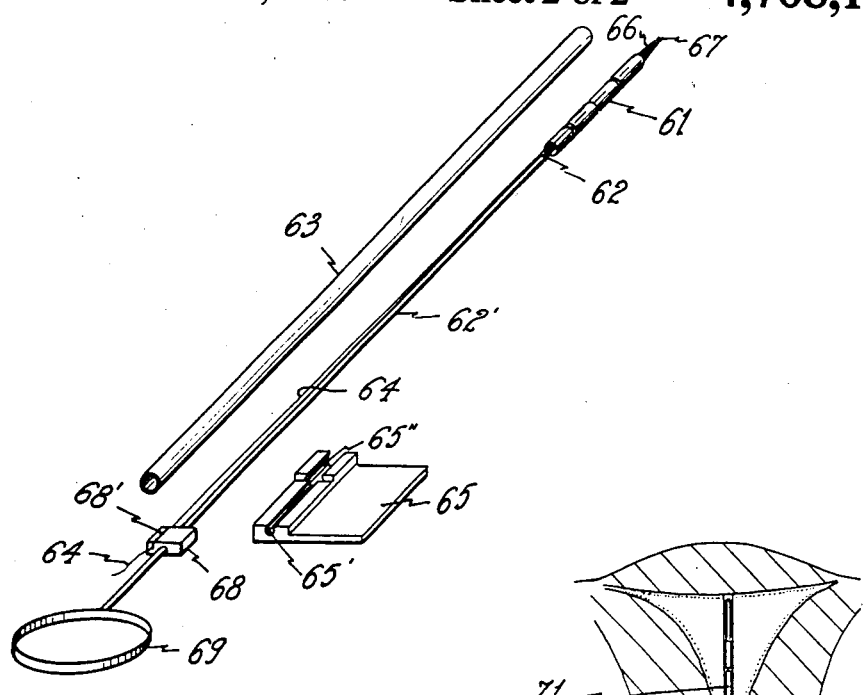
FIG. 6 is an exploded view, in perspective, of a preferred embodiment of a device for inserting an IUD into the uterus.

Referring now particularly to FIG. 1, an IUD 11 is made of a series of hollow members 12, made in a material which is active in the uterine cavity, open at both ends and arranged in a sequence in order to form a longitudinal passage 13, and a thread 14, passing through said longitudinal passage 13. At one end of the passage 13, the thread 14 is secured to a stop means 15, and is provided at the other end of the passage with a loop 16 allowing cooperation with a split needle. Loop 16 is provided with a knot 17 constituting retaining means in the uterine tissue.

Stop means 15 ensures. the retention of the hollow members and so the consistency of the IUD once the retaining device 17 has been inserted into the uterine tissue. The distance between the retaining device 17 and the stop means 15 is choosen in order to allow a loose connection between the members 12, so that the IUD does not become a rigid unit.

According to the embodiment of FIG. 2, an IUD 21 is made of a series of hollow members 22 made of a material active in the uterine cavity, butt joined in order to form a longitudinal passage 23, and a thread 24, passing through the said longitudinal passage 23. At one end, thread 24 is provided with a loop 26 for cooperation with a split needle, and a knot 27 is provided in the said loop and makes the retaining device in the uterine tissue. Loop 25 of thread 24, knotted around the distal hollow member, with regard to the retaining device 27 in the uterine tissue, constitutes a stop means, while loop 28 knotted around the closest hollow member constitutes a second stop means, the other hollow members being retained between these two stop means.

According to the embodiment of FIG. 3, an IUD 31 is made of a series of hollow members 32 butt-joined to form a longitudinal passage 33 allowing passing through of a needle, the connection between the hollow members 32 being ensured by links 34. The upper link 34' is connected to a thread 36 which ends in a retaining tipped device 37. This tip is provided at its lower end with a pin 38 provided for cooperating with the lumen of a hollow needle without sharp edges, the latter being used for inserting the retaining device into the uterine tissue.

The several IUDs described hereabove can be inserted into the uterus by means of a device as represented in FIG. 4. In this figure, the inserting device 40 and the IUD 41 are represented approximately at a 1/1 scale, at least for what regards cross-sections and one can notice immediately the very small cross sectional bulkiness of the whole unit, allowing very easy passing through the narrow cervical canal, even for women who never became pregnant. As an example, during experiments with this instrument, use was made of an inserting device of only 3 millimeter in outer diameter, which is a lot smaller than the diameter of most insertors, the diameter of which is at about 5-6 mm, and even more.

The inserting device 40 consists of a needle 42 provided for cooperating with a retaining means in the uterine tissue making part of the IUD, and a protecting member 43 for the needle and at the same time receiving member for the IUD. The needle 42 passes through longitudinal passage of the IUD 41. In the example shown, the IUD is as represented in FIG. 2. The needle 42 is split at its forward tip for receiving loop 46 provided with a retaining member 47 in the uterine tissue. The member 43 for protecting the needle and receiving the IUD is tubular, and its internal cross section substantially corresponds with the cross section of the IUD 41. A thread 44 assembling the members of the IUD extends further backward beyond the IUD in the protecting member 43 and goes out the lower part thereof, where it is fixed at the external surface of the said protecting member 43 by means of a clip 45. This connection of the thread to the protecting member precludes the needle to project beyond the protecting member 43. Moreover, the needle 42, the rear part of which comprises actuating means 42', is provided with a stop means 48 for cooperating with the protecting member 43 in order to limit the penetration depth of the needle 42 into the uterine wall. A thumb piece 49 provided at the end of the needle allows easy manipulation of this latter.

Figure 8:
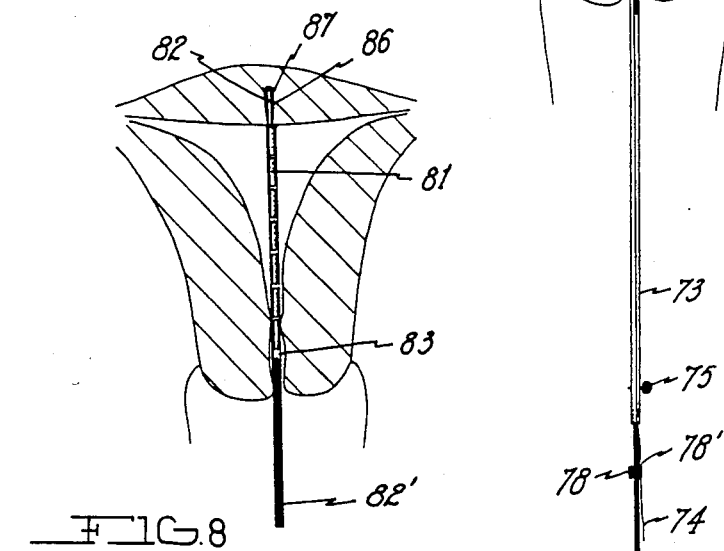
FIG. 8 is a partial view of an inserting device, inserted into the uterus, after the needle has penetrated into the uterine wall.
Figure 7:
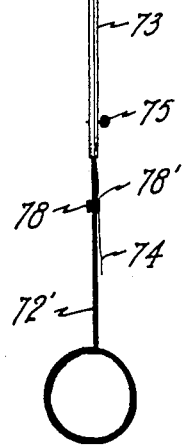
FIG. 7 represents another embodiment of an inserting device according to the invention, inserted into the uterus.

During the insertion of the IUD into the uterus, the needle 42 and the protecting member 43 are kept steady together by the practitioner, the thread 44 being taut. The protecting member is inserted within the cervical canal and passes through easily, due to its small diameter. The unit is then pushed foreward, the protecting member 43 and the needle 42 still being kept jointly, until the front end of the protecting member comes into contact with the fundus of the uterus. FIG. 7 represents this position, in fact in relation with another inserting device. Clip 45 is then withdrawn and the needle 42, with the interconnected retaining member 47, is pushed into the uterine muscle until the stop means 48 comes into contact with the protecting member 43. Such position is illustrated in FIG. 8. The needle 42 is then withdrawn, leaving the retaining device 47 in the tissue of the uterus, and the protecting member 43 is then withdrawn from the uterus. From this time, the retaining device 47, retained in the uterine tissue, holds the IUD which freely slides out of the protecting member 43.

In this embodiment, the interconnection of the needle 42 and the protecting member 43 with regard to a rearward movement of the needle within the protecting member, is obtained by these parts being simultaneously taken in hand by the practioner. Interconnection of the needle 42 and the protecting member 43, with regard to forward movement of the needle, is obtained by the tension of thread 44 kept in place by clip 45.

In a simplified embodiment, one could provide that the tension on the thread also results from the holding by the practioner, who simultaneously keeps the end of the protecting member 43, with the thread 44 folded over the outer side of this protecting member, and the part of the needle 42 adjacent to the end of the protecting member. From that point of view, the clip 45 is superfluous.

In another embodiment, as partly shown in FIG. 5, one can provide a clip 55 which keeps the thread 54 along the outer surface of the protecting member 53 and simultaneously cooperates with the stop means 58 for interconnecting needle 52 and protecting member 53. Interconnection of the needle 52 to the protecting member 53, and of the latter to the thread 54, on one hand precludes the needle to project beyond the protecting member and, on the other hand, ensures cooperation of the needle and the retaining device in the uterine tissue, the thread being kept taut for this purpose. In this latter case the practitioner has only to care for the correct insertion of the device in the uterus.

Turning now to FIG. 6 which represents a preferred embodiment of the invention, the inserting device is made of a needle 62, the back part of which, constituting actuating member 62', ends with a ring 69, a protecting member 63 and a clip 65. A stop 68 is provided on the needle, for limiting the backward movement of the protecting member 63 to the distance required for freeing the length of the needle tip intended for penetration into the uterine tissue. This stop 68 has a slot 68'. Clip 65 includes a housing 65' for cooperating with the needle 62, extending as a housing 65" intended for cooperation with the protecting member 63. Engagement of the clip 65 respectively with the needle 62 and the protecting member 63 ensures interlocking of the needle and the protecting member.

This inserting device has great advantages, both as to manufacture and use. Indeed, during manufacture, the IUD is put on the needle 62 by interlocking the loop 66 with the tip of the needle. Then, the thread 64 is taut and bound within the slot 68'. The IUD 61 is so firmly interlocked with the needle and one can, without taking special precautions for maintaining the interlocking of the IUD with the needle, complete the assembly of the device by sliding the protecting device 63 over the needle and the IUD, and by fitting the clip 65 on the assembly.

In use, both the thread end projecting outside the slot 68' and the clip 65 are easily accessible and allow easy handling of the device.

The inserting device shown in FIG. 7 is substantially similar to the one of FIG. 6, with the difference that the clip 65 is substituted therein by a pin 75 passing through the protecting member 73 and the needle 72, at the level of the actuating member 72' thereof. In FIG. 7, the inserting device has passed the cervical canal and has been brought into contact with the fundus of the uterus, however without the interlocking between the protecting member 73 and the needle 72 having been released, nor the thread 74 having been released from the slot 78'.

FIG. 8 shows the following step for placing the IUD, after release of the thread and unlocking of the protecting member 83 from the needle 82. The tip of the needle 82, interlocked with the loop 86 and the retaining member 87, is pushed into the uterine tissue. So, the protecting member 83 moves rearward onto the needle, till it engages the stop provided thereon. So, the penetration of the needle into the uterine tissue is limited. When the needle 82 is withdrawn, the retaining device 87, interlocked with the loop 86, remains in the uterine tissue and holds in place the IUD 81 when the protecting member 83 is also withdrawn.

One comes so back in the position shown in FIG. 9 where an IUD 91 interlocked with a thread 94 is held in the uterus by the action of the retaining member 97 inserted in the uterine tissue. Thread 94 is then cut to the desired length.

All the IUDs represented in the drawings consist of hollow tubular members. This shape is the one which is the easiest to manufacture. It is obvious that the invention is not limited to this tubular shape of the hollow members.

In general these members are made from copper. In this regard, it is to be noted that existence of a tubular passage and the fact that the members are rather loosely interconnected, ensures that these members are active both by the outer and the inner surface. So, one get a high active surface for each member. Further, the design of the IUD of the invention allows use of a copper amount well above the one of the existing devices. These two parameters ensure great effectiveness of the device.

Moreover, when the members are merely stringed on a thread, as represented in FIGS. 1 and 2, one or several members can be made of consumable material, for instance a substance releasing a treating agent in the uterus. Using out of one member does not break the chain, and the other members remain in place in the uterus after the consumable members have been used out.

According to a preferred embodiment of the invention, the IUD 91 is of sufficient length to extend up to within the cervical canal as shown in FIG. 9, in order to allow copper action also in this portion of the uterus. The action of the copper at that point of the reproductive tract is indeed important from a contraceptive point of view and also from a prophylactic point of view (action against gonococeal infection).

The invention has been described and illustrated merely by way of examples which are in no way restrictive. Numerous changes in its conception may be made without departing from the spirit of the invention.

What is claimed is:

1. An intrauterine contraceptive device for a uterus, comprising:
    a retaining means for anchoring said intrauterine contraceptive device in fundal tissue of said uterus;
    a fixing means integral with said retaining means for inserting said retaining means in said fundal tissue; and
    a plurality of hollow members affixed to said fixing means to form a non-rigid assembly, each of said plurality of hollow members having a passage therethrough and affixed to said fixing means end-to-end whereby said non-rigid assembly has a longitudinal passage formed therethrough, and wherein said plurality of hollow members are fabricated of a material active within said uterus to prevent pregnancy.

2. An IUD according to claim 1, characterized in that the hollow members are interconnected by means of links achieving a non rigid assembly, and that at least one of the hollow members or the links is attached to the fixing means provided with the retaining means to the uterus.

3. The intrauterine contraceptive device according to claim 1 wherein said fixing means includes a thread means for assembling said plurality of hollow members to form said non-rigid assembly by passing said thread through said passages thereof, and wherein said intrauterine contraceptive device further comprises a stop means integral with said thread distal from said retaining means for retaining said plurality of hollow members on said thread. into the uterine tissue 4. An IUD according to claim 3 characterized in that the stop means on the thread is made by the thread being affixed to the remotest hollow member remotest from the retaining device in the uterine tissue.

5. An IUD according to claim 4 characterized in that a second stop means is formed on the thread by fixing the thread to the hollow member closest to the retaining device in the uterine tissue, the interval between the two stop means allowing a loose interconnection of the hollow members.

6. The intrauterine contraceptive device according to claim 3 wherein said thread means extends beyond said stop means in a direction away from said retaining means whereby traction is applied to said retaining means by force applied to said extending thread means.

7. The intrauterine contraceptive device according to claim 6 further comprising:

a protecting member for slidably receiving therein said intrauterine contraceptive device, and an actuating member having a needle disposed at one end thereof, said actuating member movable within said protecting member to cause said needle to engage said fixing means proximal said retaining means by passing through said longitudinal passage of said non-rigid assembly of hollow members, whereby further movement of said actuating member causes insertion of said retaining means in said fundal tissue by means of said needle.

8. The intrauterine contraceptive device according to claim 7 further comprising an actuating member stop means provided on said actuating member distal said needle for limiting movement of said actuating member within said protective member and a means for blocking said thread means extending beyond said stop means whereby a segment of said thread means is retained externally of said protecting member.

9. The intrauterine contraceptive device according to claim 8 wherein said actuating member stop means includes a slot formed therein for retaining said thread means, said slot constituting said means for blocking said thread means.

10. The intrauterine contraceptive device according to claim 7 further comprising a means for releasably affixing said protecting member and said actuating member in combination.

11. The intrauterine contraceptive device according to claim 1 wherein at least one of said plurality of hollow members is fabricated of a material which causes release of an active substance for prophylactic treatment of said uterus.

12. The intrauterine contraceptive device according to claim 1 wherein said plurality of hollow members further comprise copper tubular members.

* * * * *